(12) United States Patent
Capote et al.

(10) Patent No.: US 11,432,896 B2
(45) Date of Patent: Sep. 6, 2022

(54) FLEXIBLE SKIN BASED PATIENT TRACKER FOR OPTICAL NAVIGATION

(71) Applicant: Medtronic Navigation, Inc., Louisville, CO (US)

(72) Inventors: Marco Capote, Boulder, CO (US); Matthew F. Dicorleto, Boulder, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 248 days.

(21) Appl. No.: 16/572,035

(22) Filed: Sep. 16, 2019

(65) Prior Publication Data

US 2020/0008897 A1 Jan. 9, 2020

Related U.S. Application Data

(63) Continuation of application No. 14/663,034, filed on Mar. 19, 2015, now Pat. No. 10,413,377.

(51) Int. Cl.
*A61B 46/00* (2016.01)
*A61B 34/20* (2016.01)
(Continued)

(52) U.S. Cl.
CPC .............. *A61B 46/00* (2016.02); *A61B 34/20* (2016.02); *A61B 90/39* (2016.02); *A61B 2017/00951* (2013.01); *A61B 2034/2051* (2016.02); *A61B 2034/2055* (2016.02); *A61B 2046/205* (2016.02); *A61B 2090/363* (2016.02); *A61B 2090/376* (2016.02); *A61B 2090/3937* (2016.02); *A61B 2090/3945* (2016.02); *A61B 2090/3983* (2016.02); *A61B 2090/3991* (2016.02)

(58) Field of Classification Search
CPC ......... A61B 46/00; A61B 34/20; A61B 90/39; A61B 2034/2055; A61B 2046/205
See application file for complete search history.

(56) References Cited

U.S. PATENT DOCUMENTS

| 4,524,767 A | 6/1985 | Glassman |
| 5,592,939 A | 1/1997 | Martinelli |

(Continued)

FOREIGN PATENT DOCUMENTS

| DE | 102010011589 A1 | 9/2011 |
| EP | 2298215 A1 | 3/2011 |

(Continued)

OTHER PUBLICATIONS

International Preliminary Reporton Patentability dated Sep. 28, 2017 in corresponding International Application No. PCT/US2016/021304.

(Continued)

*Primary Examiner* — Jason M Ip
(74) *Attorney, Agent, or Firm* — Harness, Dickey & Pierce, P.L.C.

(57) ABSTRACT

A skin-based patient tracking apparatus for surgical navigation. The apparatus includes an adhesive layer, a plurality of surgical tracking elements, a base layer between the adhesive layer and the plurality of surgical tracking elements, and an outer layer covering the plurality of surgical tracking elements.

14 Claims, 5 Drawing Sheets

(51) Int. Cl.
*A61B 46/20* (2016.01)
*A61B 17/00* (2006.01)
*A61B 90/00* (2016.01)

(56) References Cited

U.S. PATENT DOCUMENTS

| | | |
|---|---|---|
| 5,740,808 A | 4/1998 | Panescu et al. |
| 5,913,820 A | 6/1999 | Bladen et al. |
| 6,477,400 B1 | 11/2002 | Barrick |
| 7,840,253 B2 | 11/2010 | Tremblay et al. |
| 8,108,025 B2 | 1/2012 | Csavoy et al. |
| 8,238,631 B2 | 8/2012 | Hartmann et al. |
| 8,311,611 B2 | 11/2012 | Csavoy et al. |
| 8,467,852 B2 | 6/2013 | Csavoy et al. |
| 8,548,563 B2 | 10/2013 | Simon et al. |
| 10,413,377 B2 | 9/2019 | Capote et al. |
| 2004/0147839 A1 | 7/2004 | Moctezuma de la Barrera et al. |
| 2005/0085714 A1 | 4/2005 | Foley et al. |
| 2008/0269600 A1 | 10/2008 | Csavoy et al. |
| 2008/0292131 A1* | 11/2008 | Takemoto ............ G06T 7/80 382/100 |
| 2009/0177077 A1 | 7/2009 | Piferi et al. |
| 2010/0160771 A1 | 6/2010 | Gielen et al. |

FOREIGN PATENT DOCUMENTS

| | | |
|---|---|---|
| WO | 0180738 A1 | 11/2001 |
| WO | 2014032171 A1 | 3/2014 |

OTHER PUBLICATIONS

International Search Report and Written Opinion dated Jun. 9, 2016 for PCT/US2016/021304 which claims benefit of U.S. Appl. No. 14/663,034, filed Mar. 19, 2015.

U.S. Appl. No. 14/663,034, U.S. Pat. No. 10,413,377, filed Mar. 19, 2015, Capote, et al.

* cited by examiner

FLEXIBLE SKIN BASED PATIENT TRACKER FOR OPTICAL NAVIGATION

CROSS-REFERENCE TO RELATED APPLICATIONS

This application is a continuation of U.S. application Ser. No. 14/663,034 filed on Mar. 19, 2015, now U.S. Pat. No. 10,413,377 issued on Sep. 17, 2019, the entire disclosure of which is incorporated herein by reference.

FIELD

The present disclosure relates to a flexible skin-based patient tracking apparatus for optical surgical navigation.

BACKGROUND

This section provides background information related to the present disclosure, which is not necessarily prior art.

In an anatomy, such as a human anatomy, various anatomical portions and functions may be damaged or require repair after a period of time. The anatomical portion or function may be injured due to wear, aging, disease, or exterior trauma. To assist the patient, a procedure may be performed that may require access to an internal region of the patient through an incision. Due to exterior soft tissue, visualization of portions of the interior of the anatomy may be difficult or require a large opening in the patient.

Image data may be required of a patient to assist in planning, performing, and post-operative analysis of a procedure. For example, magnetic resonance image data can be acquired of the patient to assist in diagnosing and planning a procedure. The image data acquired of the patient can also be used to assist in navigating various instruments relative to the patient while performing a procedure.

It is known to fixedly interconnect fiducial markers or tracking devices with a patient while imaging the patient and substantially using the fiducial markers that are imaged in the image data to correlate or register the image data to a patient space and the tracking devices for subsequent tracking. The fiducial markers and/or tracking devices are sometimes invasively fixed directly to the patient. While such fiducial markers and/or tracking devices are suitable for their intended use, they are subject to improvement. For example, it may be desirable to: minimize the invasiveness of the fiducial markers and/or tracking devices on the patient; not limit registration to the specific discrete locations of implanted fiducial markers; overcome issues presented when the fiducial markers and/or tracking devices are obscured during surgery; and generally increase the accuracy of the fiducial markers and/or tracking devices. An improved patient tracker would also be desirable. The present teachings are directed to an improved patient tracker that may be an improved fiducial as well.

SUMMARY

This section provides a general summary of the disclosure, and is not a comprehensive disclosure of its full scope or all of its features.

The present teachings provide for a skin-based patient tracking apparatus for surgical navigation. The apparatus generally includes an adhesive layer, a plurality of surgical tracking elements, a base layer between the adhesive layer and the plurality of surgical tracking elements, and an outer layer covering the plurality of surgical tracking elements.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
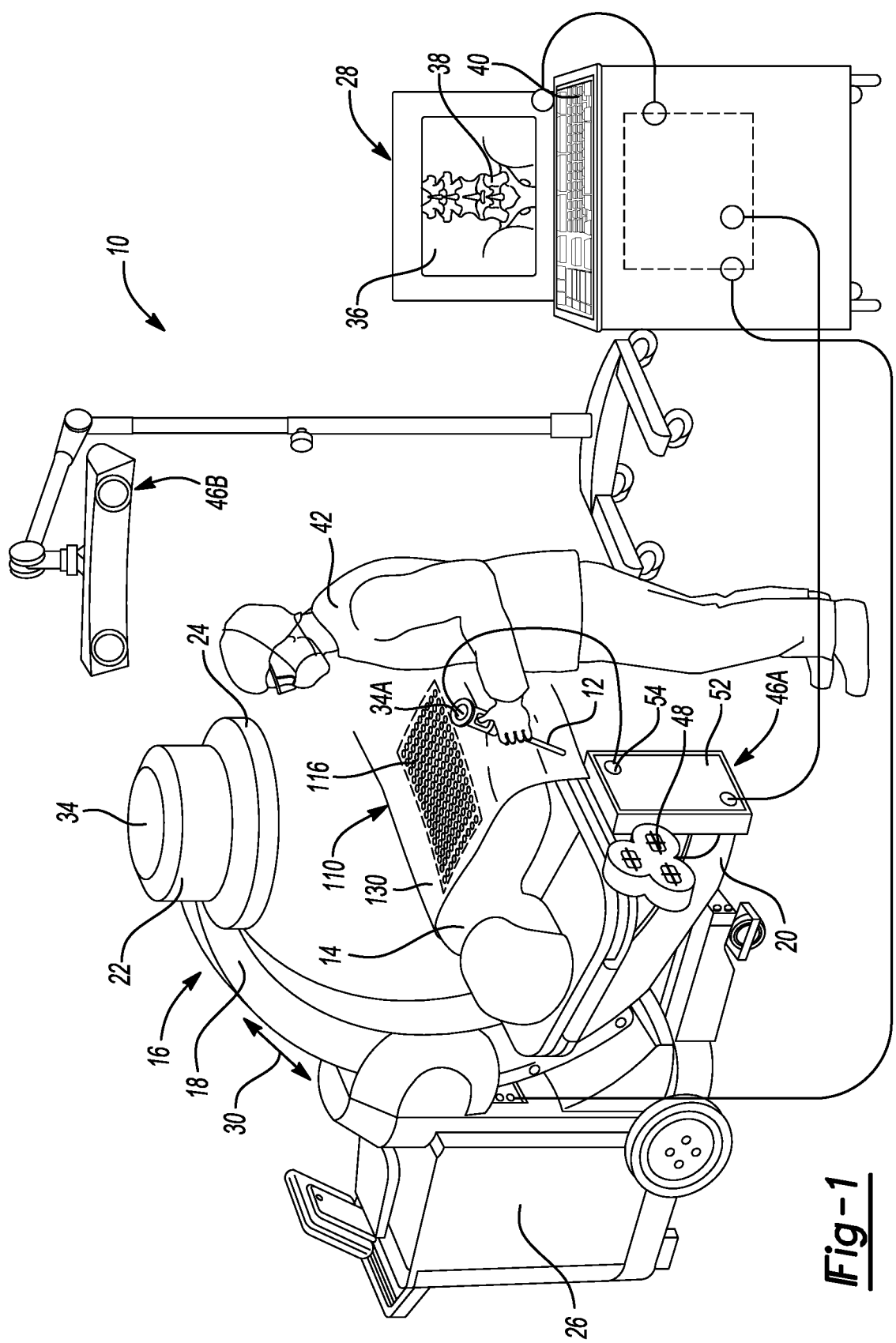
FIG. 1 is an environmental view of a surgical navigation system according to the present teachings.

With initial reference to FIG. 1, a surgical navigation system according to the present teachings for use during various procedures is generally illustrated at reference numeral 10. The system 10 can be used to track location of a device 12 relative to a patient 14 to assist in the implementation of, or the performance of, any suitable surgical procedure. The device 12 can be any suitable surgical device, such as any suitable probe including a pointer probe, a catheter, a needle, a lead, an electrode implant, a cutting instrument, etc. More specific examples include ablation catheters, deep brain stimulation (DBS) leads or electrodes, microelectrode (ME) leads, electrodes for recording, etc. Moreover, the navigated device 12 may be used in any region of the body, in addition to the back as illustrated. The navigation system 10 and the various devices 12 may be used in any appropriate procedure, such as a minimally invasive procedure, arthroscopic procedure, percutaneous procedure, stereotactic procedure, or an open procedure.

Although an exemplary navigation system 10 including an imaging system 16 is discussed herein, one skilled in the art will understand that the present teachings are merely for clarity of the present discussion and exemplary purposes, and that any appropriate imaging system, navigation system, patient specific data, and non-patient specific data can be used. For example, the intraoperative imaging system can include an MRI imaging system, such as the PoleStar® MRI imaging system or an O-Arm® imaging system sold by Medtronic, Inc. having a place of business in Minnesota, USA. It will be understood that the navigation system 10 can incorporate or be used with any appropriate preoperatively or intraoperatively acquired image data.

The navigation system 10 can include the optional imaging device 16 that is used to acquire pre-, intra-, or post-operative, including real-time, image data of the patient 14.

In addition, data from atlas models can be used to produce images for navigation, though they may not be patient images. Although, atlas models can be morphed or changed based upon patient specific information. Also, substantially imageless systems can be used, such as those disclosed in U.S. patent application Ser. No. 10/687,539, filed Oct. 16, 2003, now U.S. Pat. App. Pub. No. 2005/0085714, entitled "METHOD AND APPARATUS FOR SURGICAL NAVIGATION OF A MULTIPLE PIECE CONSTRUCT FOR IMPLANTATION", incorporated herein by reference. Various systems can use data based on determination of the position of various elements represented by geometric shapes.

The optional imaging device 16 is, for example, a fluoroscopic X-ray imaging device that may be configured as a C-arm 18 having an X-ray source 20, an X-ray receiving section 22, an optional calibration and tracking target 24 and optional radiation sensors. The calibration and tracking target 24 includes calibration markers (not illustrated). Image data may also be acquired using other imaging devices, such as those discussed above and herein.

An optional imaging device controller 26 may control the imaging device 16, such as the C-arm 18, which can capture the X-ray images received at the receiving section 22 and store the images for later use. The controller 26 may also be separate from the C-arm 18 and can be part of, or incorporated into, a workstation 28. The controller 26 can control the rotation of the C-arm 18. For example, the C-arm 18 can move in the direction of arrow 30 and/or rotate about the patient 14 in any suitable manner, allowing anterior or lateral views of the patient 14 to be imaged. The movements of the imaging device 16, such as the C-arm 18, can be tracked with a tracking device 34. As discussed herein, the tracking device 34, according to various embodiments, can be any appropriate tracking device to work with any appropriate tracking system (e.g. optical, electromagnetic, acoustic, etc.). Therefore, unless specifically discussed otherwise, the tracking device 34 can be any appropriate tracking device.

In the example of FIG. 1, C-arm 18 can be positioned in any suitable manner to permit images of the patient 14 to be taken from multiple directions or in multiple planes. An example of a fluoroscopic C-arm X-ray device that may be used as the optional imaging device 16 is the "Series 9600 Mobile Digital Imaging System," from GE Healthcare, (formerly OEC Medical Systems, Inc.) of Salt Lake City, Utah. Other exemplary fluoroscopes include bi-plane fluoroscopic systems, ceiling mounted fluoroscopic systems, cath-lab fluoroscopic systems, fixed C-arm fluoroscopic systems, isocentric C-arm fluoroscopic systems, three-dimensional (3D) fluoroscopic systems, intraoperative O-Arm™ imaging systems, etc.

The C-arm imaging system 18 can be any appropriate system, such as a digital or CCD camera, which are well understood in the art. Two-dimensional fluoroscopic images that may be taken by the imaging device 16 are captured and stored in the C-arm controller 26. Multiple two-dimensional images taken by the imaging device 16 may also be captured and assembled to provide a larger view or image of a whole region of the patient 14, as opposed to being directed to only a portion of a region of the patient. For example, multiple image data or sets of data of a patient's back, leg, cranium, and brain may be appended together to provide a full view or complete set of image data of the back, leg, or brain that can be later used to follow contrast agent, such as bolus or therapy tracking. The multiple image data can include multiple two-dimensional (2D) slices that are assembled into a 3D model or image.

The image data can then be forwarded from the C-arm controller 26 to the navigation computer and/or processor controller or workstation 28 having a display device 36 to display image data 38 and a user interface 40. The workstation 28 can also include or be connected to an image processor, a navigation processor, and a memory to hold instructions and data. The workstation 28 can also include an optimization processor that assists in a navigated procedure. It will also be understood that the image data is not necessarily first retained in the controller 26, but may also be directly transmitted to the workstation 28. Moreover, processing for the navigation system and optimization can all be done with single or multiple processors all of which may or may not be included in the workstation 28.

The workstation 28 provides facilities for displaying the image data 38 as an image on the display device 36, saving, digitally manipulating, or printing a hard copy image of the received image data. The user interface 40, which may be a keyboard, mouse, touch pen, touch screen or other suitable device, allows a physician or user 42 to provide inputs to control the imaging device 16, via the C-arm controller 26, or adjust the display settings of the display 36. The workstation 28 may also direct the C-arm controller 26 to adjust the C-arm 18 to obtain various two-dimensional images in different planes in order to generate representative two-dimensional and three-dimensional images.

While an exemplary optional imaging device 16 is shown in FIG. 1, any other alternative 2D, 3D or 4D imaging modality may be used. For example, any 2D, 3D or 4D imaging device, such as isocentric fluoroscopy, bi-plane fluoroscopy, ultrasound, computed tomography (CT), multi-slice computed tomography (MSCT), magnetic resonance imaging (MRI), positron emission tomography (PET), optical coherence tomography (OCT) (a more detailed discussion on optical coherence tomography (OCT), is set forth in U.S. Pat. No. 5,740,808, issued Apr. 21, 1998, entitled "Systems And Methods For Guiding Diagnostic Or Therapeutic Devices In Interior Tissue Regions" which is hereby incorporated by reference). Intra-vascular ultrasound (IVUS), intraoperative CT, single photo emission computed tomography (SPECT), planar gamma scintigraphy (PGS). Additional imaging systems include intraoperative MRI systems such as the PoleStar® MRI imaging system. Further systems include the O-Arm® imaging system. The images may also be obtained and displayed in two, three or four dimensions. In more advanced forms, four-dimensional surface rendering regions of the body may also be achieved by incorporating patient data or other data from an atlas or anatomical model map or from pre-operative image data captured by MRI, CT, or echocardiography modalities.

Image datasets from hybrid modalities, such as positron emission tomography (PET) combined with CT, or single photon emission computer tomography (SPECT) combined with CT, could also provide functional image data superimposed onto anatomical data to be used to confidently reach target sights within the patient 14. It should further be noted that the optional imaging device 16, as shown in FIG. 1, provides a virtual bi-plane image using a single-head C-arm fluoroscope as the optional imaging device 16 by simply rotating the C-arm 18 about at least two planes, which could be orthogonal planes to generate two-dimensional images that can be converted to three-dimensional volumetric images. By acquiring image data in more than one plane, an icon representing the location of an impactor, stylet, reamer driver, taps, drill, DBS electrodes, ME electrodes for recording, probe, or other instrument, introduced and advanced in the patient 14, may be superimposed in more than one view on display 36 allowing simulated bi-plane or even multi-plane views, including two and three-dimensional views.

With continuing reference to FIG. 1, the navigation system 10 can further include a tracking system, such as, but not limited to, an electromagnetic (EM) tracking system 46A or an optical tracking system 46B. Either or both can be used alone or together in the navigation system 10. Moreover, discussion of the EM tracking system 46A can be understood to relate to any appropriate tracking system. The optical tracking system 46B can include the Stealthstation® Treatment Guidance System including the Treon® Navigation System and the Tria® Navigation System, both sold by Medtronic Navigation, Inc. Other tracking systems include acoustic, radiation, radar, infrared, etc.

The EM tracking system 46A includes a localizer, such as a coil array 48 and/or second coil array (not shown), a coil array controller 52, a navigation probe interface 54, a device 12 (e.g. catheter, needle, pointer probe, or instruments, as discussed herein), and can include a dynamic reference frame including a tracking device, such as patient tracking apparatus 110, which is described herein as an optical tracking apparatus, but may be an electromagnetic tracking apparatus as one skilled in the art will appreciate. An instrument tracking device 34A can also be associated with, such as fixed to, the device 12 or a guiding device for an instrument.

The tracking devices 34 and 34A, or any other tracking device as discussed herein, can include a sensor, a transmitter, or combinations thereof. The tracking devices 34 and 34A can be either EM tracking devices or optical tracking devices, such as reflective tracking arrays. Further, the tracking devices 34/34A can be wired or wireless to provide a signal emitter or receiver within the navigation system. For example, the tracking devices 34 and 34A can include an electromagnetic coil to sense a field produced by the localizing array 48. Nevertheless, one will understand that the tracking devices 34 and 34A can receive a signal, transmit a signal, or combinations thereof to provide information to the navigation system 10 to determine a location of the tracking devices 34 and 34A. The navigation system 10 can then determine a position of the instrument or tracking device 34A to allow for navigation relative to the patient and patient space.

It should further be noted that the entire tracking system 46A, 46B or parts of the tracking system 46A, 46B may be incorporated into the imaging device 16, including the workstation 28. Incorporating the tracking system 46A, 46B may provide an integrated imaging and tracking system. This can be particularly useful in creating a fiducial-less system. Moreover, fiducial marker-less systems can include a tracking device and a contour determining system, including those discussed herein. Any combination of these components may also be incorporated into the imaging system 16, which again can include a fluoroscopic C-arm imaging device or any other appropriate imaging device.

The EM tracking system 46A uses the coil arrays 48 to create an electromagnetic field used for navigation. The coil arrays 48 can include a plurality of coils that are each operable to generate distinct electromagnetic fields into the navigation region of the patient 14, which is sometimes referred to as patient space. Representative electromagnetic systems are set forth in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference. Further operation of the EM tracking system 46A is provided in U.S. Pat. No. 8,467,852 titled "Method and Apparatus for Performing A Navigated Procedure," which is assigned to Medtronic, Inc. and is incorporated herein by reference.

Briefly, the navigation system 10 operates as follows. The navigation system 10 creates a translation map between all points in the image data generated from the imaging device 16 which can include external and internal portions, and the corresponding points in the patient's anatomy in patient space. After this map is established, the image space is registered to patient space in any suitable manner. Examples of automatic registration are set forth in: U.S. Pat. No. 6,477,400 titled "Fluoroscopic Image Guided Orthopaedic Surgery System with Intraoperative Registration," which issued on Nov. 5, 2002 and is incorporated herein by reference; and U.S. Pat. No. 8,238,631 titled "System and Method for Automatic Registration between an Image and a Subject," which issued on Aug. 7, 2012 to Medtronic Navigation, Inc., and is incorporated herein by reference. Registration can also take place by performing the imaging with the patient tracking apparatus 110 secured to the patient as described herein.

Whenever the tracked device 12 is used, the workstation 28 in combination with the optical tracking system 46B (or optionally the EM tracking system 46A) uses the translation map to identify the corresponding point on the image data or atlas model, which is displayed on display 36. This identification is known as navigation or localization. An icon representing the localized point or instruments is shown on the display 36 within several two-dimensional image planes, as well as on three and four dimensional images and models.

To enable navigation, the navigation system 10 must be able to detect both the position of the patient's anatomy as determined using the patient tracking apparatus 110, for example, in the manner described herein, and the position of the device 12 or an attachment member (e.g., tracking device 34A) attached to the device 12. Knowing the location of these two items allows the navigation system 10 to compute and display the position of the device 12 or any portion thereof in relation to the patient 14. The tracking systems 46A and 46B are employed to track the device 12 and the anatomy of the patient 14 simultaneously.

The patient tracking apparatus 110 described herein is fixed to the patient 14 to identify the location of the patient in the navigation field. Thus, the patient tracking apparatus 110 acts as a dynamic reference frame, and may operate as a fiducial as described herein, during registration. The optical tracking system 46B continuously computes or calculate the relative position of the patient tracking apparatus 110 and the device 12 during localization and relates this spatial information to patient registration data to enable navigation of the device 12 within and/or relative to the patient 14. Navigation can include image guidance or imageless guidance.

Patient registration is the process of determining how to correlate the position of the device 12 relative to the patient 14, to the position on the diagnostic or image data. To register the patient 14, the physician or user 42 may select and store one or more particular points from the image data and then determine corresponding points on the patient's anatomy. The navigation system 10 analyzes the relationship between the points and computes a match, which correlates every point in the image data with its corresponding point on the patient's anatomy or the patient space.

The points that are selected to perform registration can be image fiducial points. The image fiducial points can be produced by the patient tracking apparatus 110 described herein. The image fiducial points are identifiable in the image data and identifiable and accessible on the patient 14. The anatomical landmarks can include individual or distinct points on the patient 14 or contours (e.g. three-dimensional contours) defined by the patient 14.

A processor, such as a processor within the workstation 28, can determine registration of the patient space to the image space. The registration can be performed according to generally known mapping or translation techniques. The registration can allow a navigated procedure using the image data.

Figure 2:
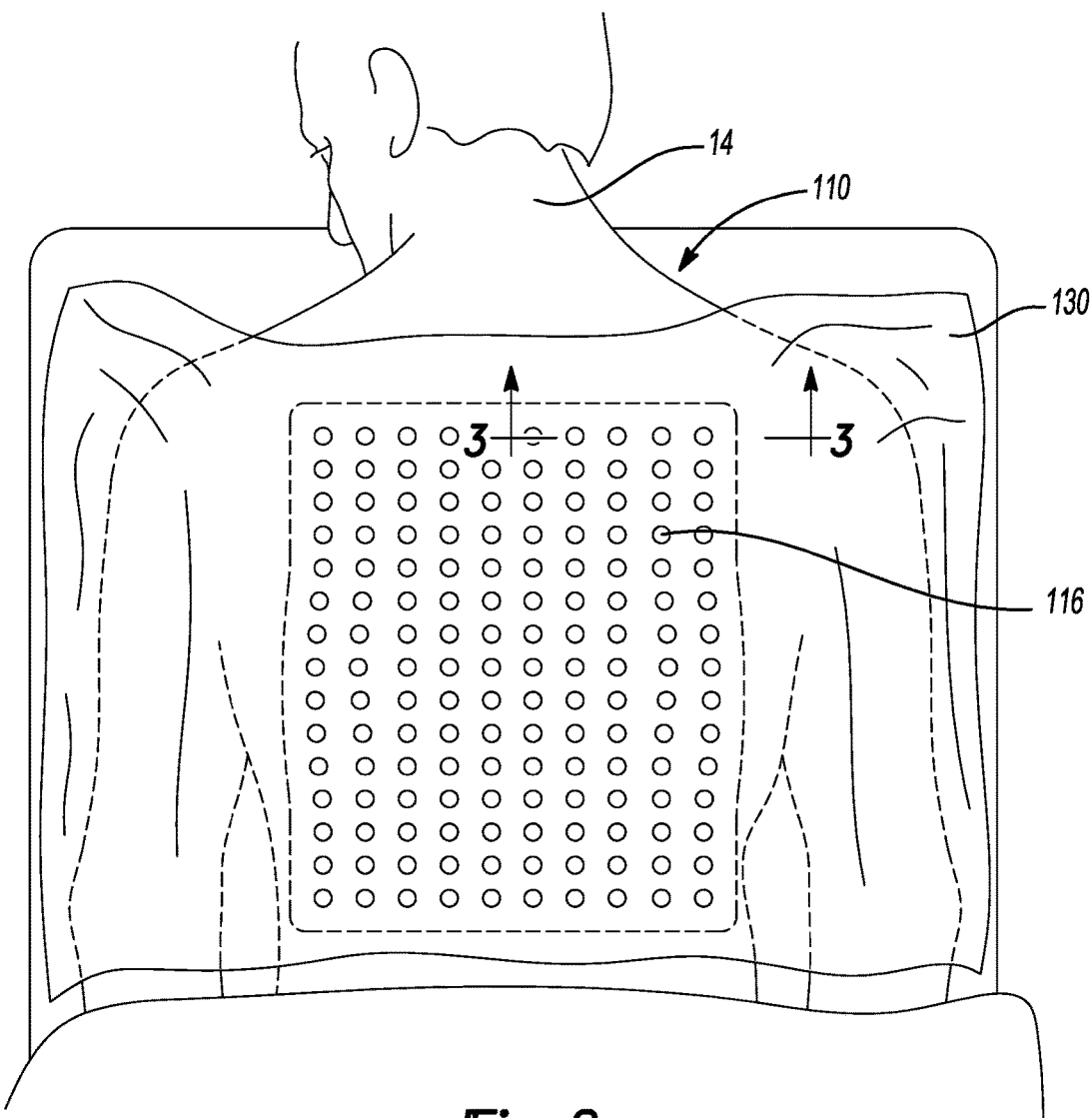
FIG. 2 illustrates a flexible skin-based patient tracker for surgical navigation according to the present teachings secured to a back of a patient.
Figure 3:
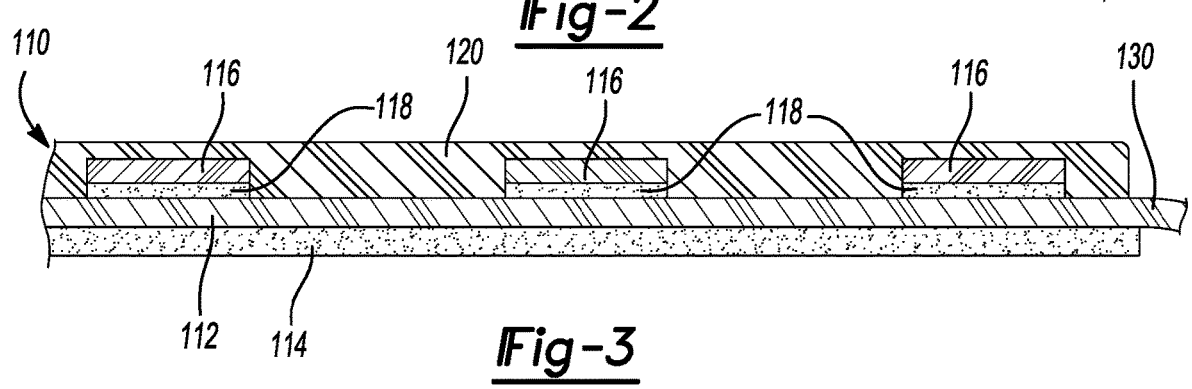
FIG. 3 is a cross-sectional view taken along line 3-3 of FIG. 2.

With continued reference to FIG. 1 and additional reference to FIGS. 2 and 3, the patient tracking apparatus 110 will now be further described. The patient tracking apparatus 110 generally includes a base layer 112, which can be made of any suitable material, to provide a flexible sheet. An adhesive layer 114 is on a first side of the base layer 112. Any adhesive suitable for securing the base layer 112 to skin can be used. While any suitable base layer 112 and adhesive layer 114 can be used, an exemplary base layer including a suitable adhesive is Tagaderm™ from 3M Corporation of Minnesota, USA. The base layer 112 can be of any suitable size or shape, such as a suitable shape to cover an area of the patient 14 to be operated on. The base layer 112 can be a portion of a surgical drape 130, as further described herein.

Secured to the base layer 112 are a plurality of tracking elements 116. The tracking elements 116 can be any suitable active or passive tracking elements, such as reflective dots or light emitting diodes (LED's) for use with the optical tracking system 46B. The tracking elements 116 can be secured to the base layer 112 in any suitable manner such as with a tracking element retention portion 118. The retention portion 118 can be any suitable adhesive, mold, or bond for securing the tracking elements 116 to the base layer 112.

Figure 4:
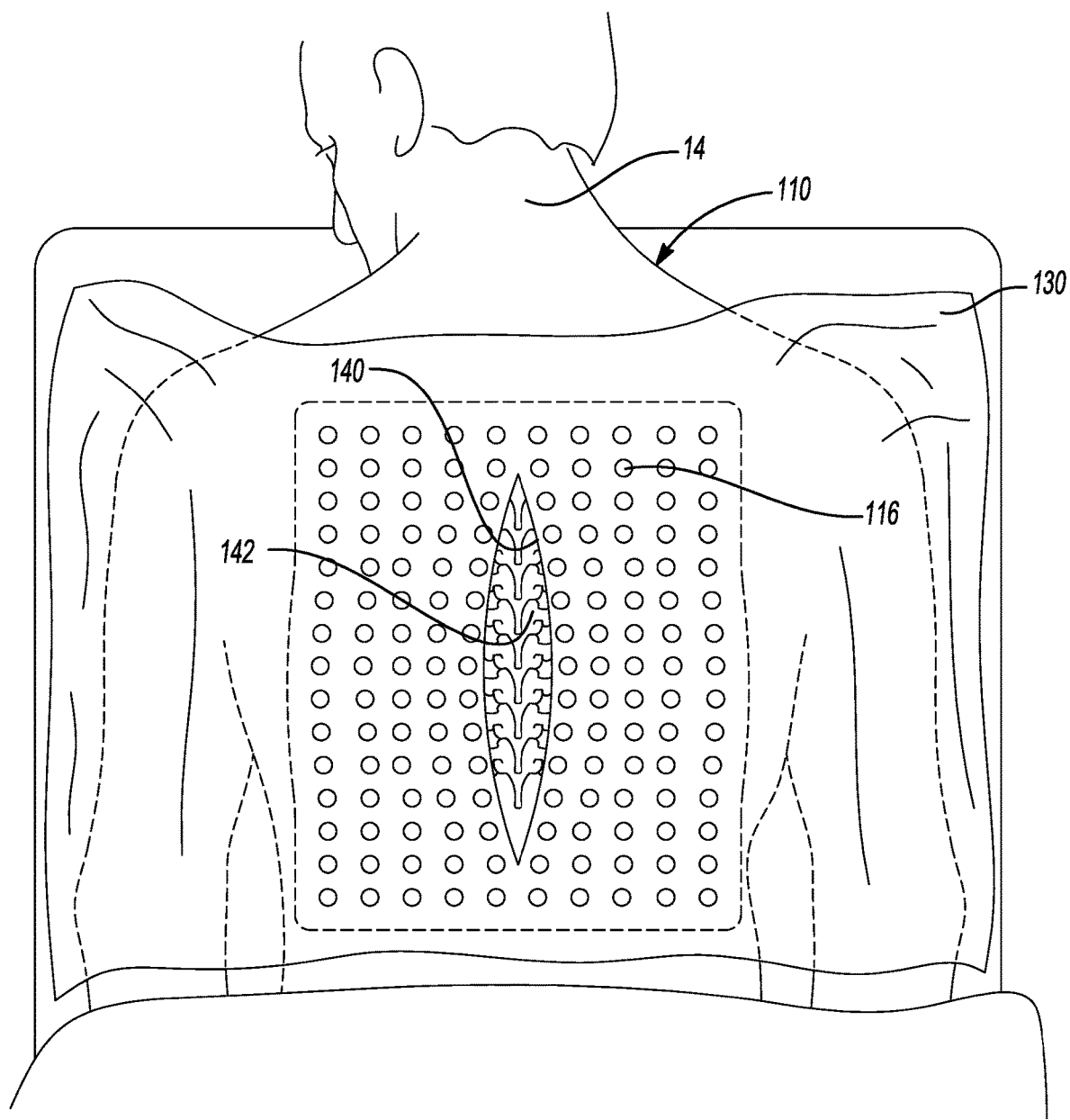
FIG. 4 illustrates the flexible skin-based patient tracker of FIG. 2 with an incision therethrough.
Figure 5:
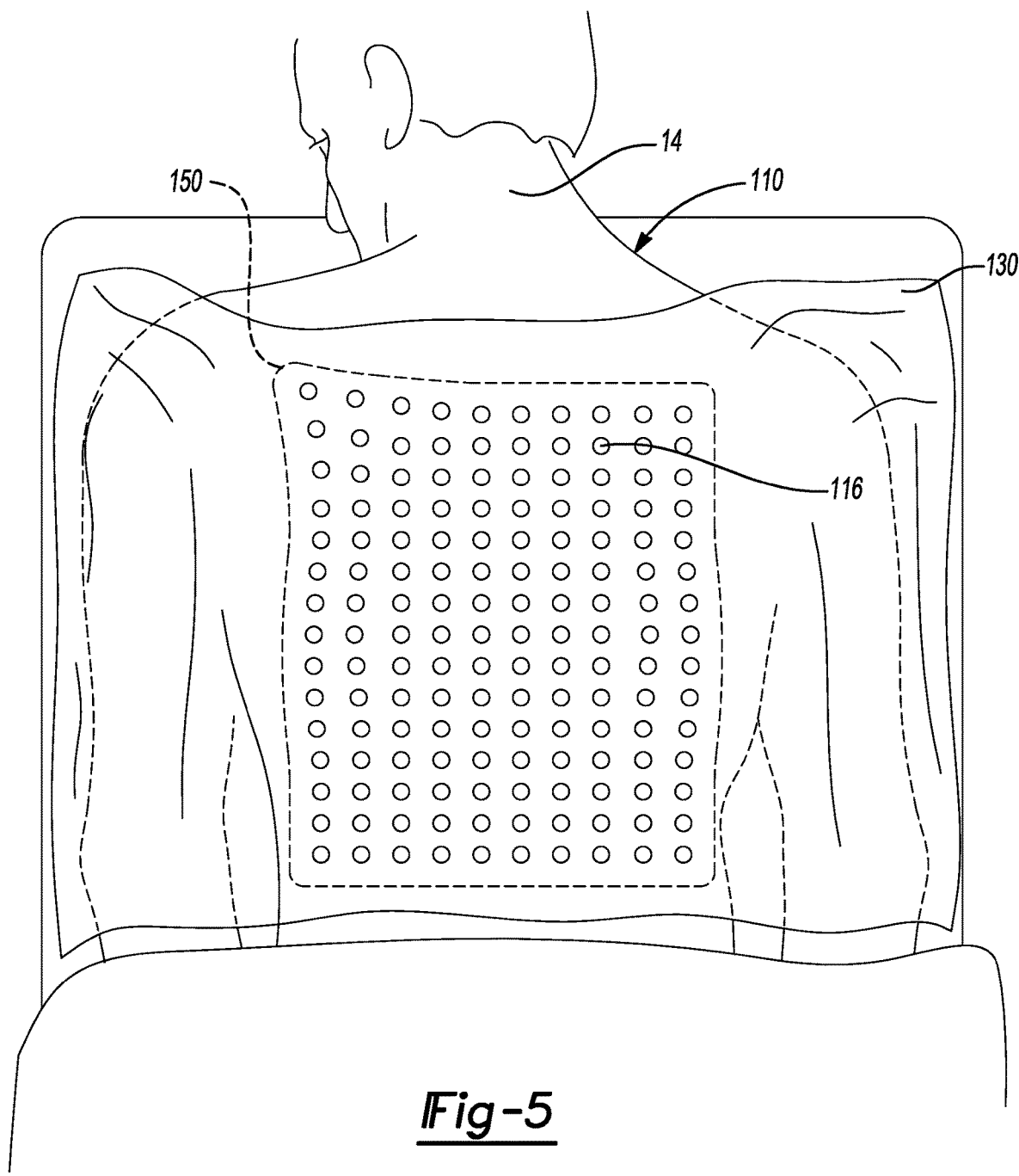
FIG. 5 illustrates the flexible skin-based patient tracker of FIG. 2 stretched at an upper left-hand corner thereof in response to movement of the patient's left shoulder.

Position of the tracking elements 116 in the patient space can be determined using the optical tracking system 46B. The tracking elements 116 can be arranged in any suitable manner, such as in a plurality or rows and columns as illustrated. Any suitable number of tracking elements 116 can be used. For example, the tracking elements 116 can be arranged in rows of ten tracking elements 116 and columns of fifteen tracking elements 116 as illustrated in FIGS. 2, 4, and 5 for a total of one hundred and fifty tracking elements 116. The tracking elements 116 can be spaced apart at any known suitable distance, such as about 2 cm.

The tracking elements 116 can be covered with an outer layer or cover 120. The cover 120 can be any suitable cover, such as any suitable transparent cover 120. The cover 120 protects the tracking elements 116 from damage, and can prevent the tracking elements 116 from becoming dirty. The cover 120 can be easily cleaned, such as by wiping with water or a suitable solvent, to allow light directed to the tracking elements by the optical tracking system 46B to be reflected by the tracking elements 116. The cover 120 can be made of any suitable material, such as a hydrophobic transparent material that, for example, repels bodily fluids and can be easily cleaned.

As illustrated in FIGS. 2, 4, and 5, for example, the patient tracking apparatus 110 can include a surgical drape 130. The surgical drape 130 can be incorporated into the patient tracking apparatus 110 in any suitable manner. For example, base layer 112 can be part of the surgical drape 130. The surgical drape 130 can extend from, and generally surround, an area of the patient tracking apparatus 110 including the tracking elements 116. The surgical drape 130 can be sterile, and can cover an area of the patient surrounding the surgical site. The surgical drape 130 can be of any suitable size or shape depending on the procedure for which the surgical drape 130 is to be used. Thus, the surgical drape 130 can be a procedure specific surgical drape.

With reference to FIGS. 2, 4, and 5, an exemplary use of the patient tracking apparatus 110 to cover, act as a fiducial, and track movement of, a patient's back during spinal surgery will now be described. Use of the apparatus 110 in conjunction with spinal surgery is illustrated and described for exemplary purposes only. The apparatus 110 can be used in conjunction with any suitable procedure at any suitable location on the patient's body. For example, the apparatus 110 can cover a portion of the patient's head during spinal surgery, and can cover a patient's chest during heart surgery.

The patient tracking apparatus 110 is secured to the patient's back over the area to be operated on with the adhesive layer 114. An incision 140 (FIG. 4) into the patient is made directly through the patient tracking apparatus 110. Due to the incision 140, the patient's skin surrounding the incision 140 will move outward from the incision 140. Because the patient tracking apparatus 110 is adhesively secured to the patient's skin, the portions of the apparatus 110 surrounding the incision 140 will also move outward, which includes the tracking elements 116. Movement of the tracking apparatus 110 can be detected by the tracking system 46B in order to track movement of the patient's skin surrounding the incision 140. With the patient's spine 142 exposed by the incision 140, any suitable spinal operation can be performed.

Any movement of the patient's back can be tracked using the patient tracking apparatus 110. For example and as illustrated in FIG. 5, if the patient's left shoulder is dipped or moved forward towards a front of the patient's body, a upper left hand corner 150 of the apparatus 110 will be stretched outward. Thus, the tracking elements 116 at and proximate to the upper left hand corner 150 will be stretched outward and a separation distance between the tracking elements 116 will increase at and proximate to the stretched upper left hand corner 150. The stretched position of the tracking elements 116 can be measured by the optical tracking system 46B.

Figure 6:
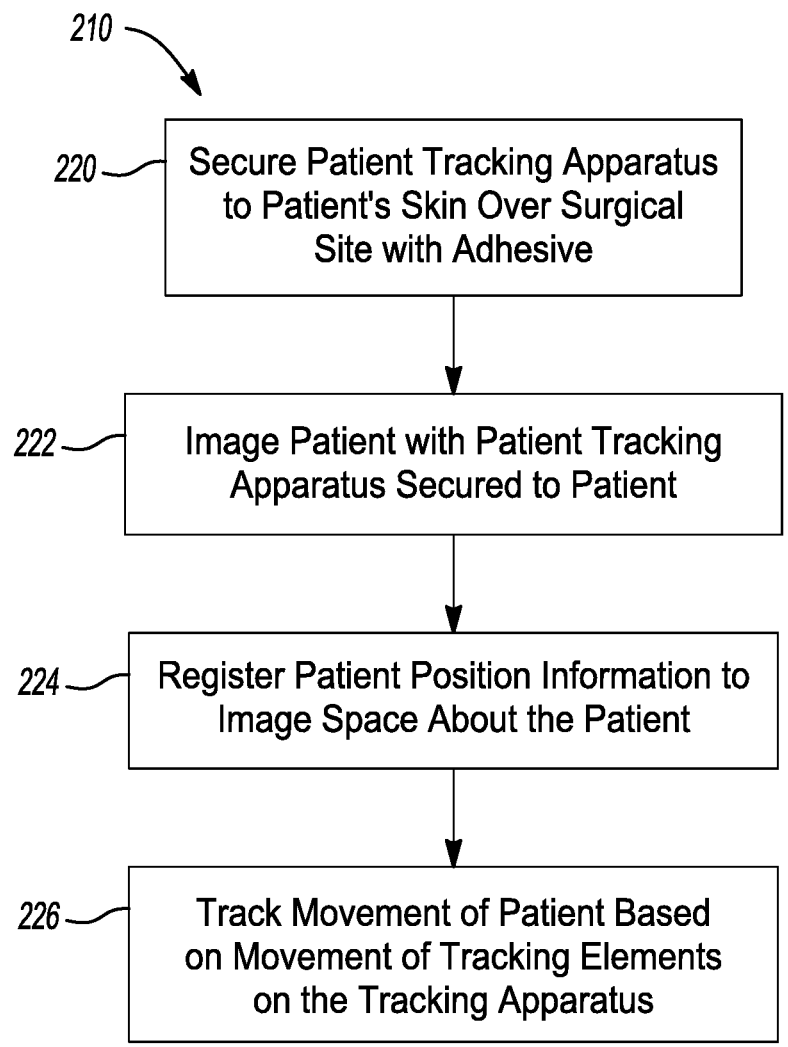
FIG. 6 illustrates a method according to the present teachings for tracking patient movement during surgery.

With additional reference to FIG. 6, a method 210 for using the patient tracking apparatus 110 will now be described. With initial reference to block 220, the patient tracking apparatus 110 is secured to the patient's skin with the adhesive layer 114 over any suitable surgical site, such as at the patient's back/spine 142. At block 222, the patient 14 is imaged in any suitable manner, such as with the imaging system 16, with the patient tracking apparatus 110 secured to the patient 14 so that the apparatus 110 acts as a fiducial. Alternatively, any other suitable fiducial can be used.

After the patient 14 is imaged, registration is performed at block 224 to register the patient position information to image space about the patient. Any suitable registration can be used, such as automatic registration as described in U.S. Pat. Nos. 6,477,400 and/or 8,238,631, or registration using fiducials. Any suitable fiducial can be used, such as the patient tracking apparatus 110.

After registration is complete, at block 226 the patient tracking apparatus 110 can be used to track position of the patient 14 within the patient space. For example, the position of each tracking element 116, and the spacing therebetween, is known and entered into any suitable processor, such as a processor of the workstation 28. Movement of the patient's skin will result in movement of the tracking elements 116. Using any suitable technique, such as averaging, changes in location of the tracking elements 116 and relative spacing therebetween can be used to identify changes in the patient's position. For example and with reference to FIG. 5, movement of the patient's left shoulder downward or forward will result in the upper left hand corner 150 of the patient tracking apparatus 110 being stretched, which will cause distances between the tracking elements 116 in the upper left hand corner 150 to increase and be stretched outward as compared to the rest of the tracking elements 116. This movement of the tracking elements 116 can be detected by the optical tracking system 46B and measured by the processor of the workstation 28, for example. Based on the measurements and using averaging, the processor can identify movement of the patient 14 and update the image data 38 displayed on the display device 36 accordingly.

Any other movement of the patient 14 can be detected in a similar manner, such as movement affecting location of the patient's spine. For example, movement of the patient's spine will result in corresponding movement of the patient's skin over the spine. Movement of the patient's skin will result in movement of the tracking elements 116 over the patient's spine, which can be detected using the optical tracking system 46B. The processor can then update the image data 38 of the patient's spine on the display device 36 accordingly.

With reference to FIG. 4, when the incision 140 is made the resulting movement of the tracking elements 116 can be taken into account when generating the image data 38 to eliminate any error. For example, upon making the incision 140 the optical tracking system 46B will measure the location of the tracking elements 116 and compare their average position both before and after the incision 140 is made. Although the tracking elements 116 will move after the incision 140 is made, the average position of the tracking elements 116 will remain the same, as will the patient's skin (assuming that the patient has not moved). Because the average position of the tracking elements 116 and the patient's skin will remain the same, the image data 38 will not need to be modified. Any patient tracking errors that may result due to making the incision 140 can advantageously be eliminated.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system for tracking movement of a patient during surgery comprising:
    a skin-based flexible patient tracking apparatus for surgical navigation including:
        a base layer having a first side and a second side;
        an adhesive layer on the first side of the base layer including an adhesive material configured to stick the skin-based flexible patient tracking apparatus to the patient's skin over a surgical site;
        a plurality of optical surgical tracking elements on the second side of the base layer;
        the base layer between the adhesive layer and the plurality of optical surgical tracking elements; and
        an outer transparent layer covering the plurality of optical surgical tracking elements;
    wherein the skin-based flexible patient tracking apparatus is formed of a material configured to be cut through with an incision during surgery to access the surgical site beneath the patient's skin; and
    wherein the skin-based flexible patient tracking apparatus is formed of the material configured to be stretched, wherein a separation distance between at least two optical tracking elements will increase in a stretched position;
    wherein the plurality of optical surgical tracking elements are configured such that an average position of the plurality of surgical tracking elements both before and after the incision is made through the skin-based flexible patient tracking apparatus and into the patient's skin as detected by a surgical tracking system corresponds to movement of the patient's skin when the patient tracking apparatus is secured over the surgical site.

2. The system of claim 1, wherein the surgical tracking elements are bonded to the base layer.

3. The system of claim 1, wherein the surgical tracking elements are secured to the base layer with an adhesive.

4. The system of claim 1, wherein the surgical tracking elements are molded to the base layer.

5. The system of claim 1, wherein the surgical tracking elements are arranged in a plurality of rows and columns.

6. The system of claim 1, further comprising a surgical drape integral with the patient tracking apparatus and sized to extend from and surrounded an area beyond the patient tracking apparatus and the surgical site.

7. The system of claim 1, wherein the base layer includes a surgical drape extending beyond a portion of the patient tracking apparatus including the plurality of surgical tracking elements.

8. The system of claim 1, wherein the average position of the plurality of surgical tracking elements is determined by a processor of the surgical tracking system.

9. A system for tracking movement of a patient during surgery comprising:
    a skin-based flexible patient tracking apparatus for surgical navigation including a plurality of surgical tracking elements and an adhesive material configured to stick the skin-based flexible patient tracking apparatus to the patient's skin over a surgical site, the skin-based flexible patient tracking apparatus formed of a material configured to be stretched and cut through with an incision during surgery to access the surgical site beneath the patient's skin;
    a drape extending from and surrounding the skin-based flexible tracking apparatus and sized to drape over an area of the patient surrounding the surgical site; and
    a surgical tracking system including a processor configured to determine an average position of the plurality of surgical tracking elements both before and after the incision is made through the skin-based flexible patient tracking apparatus and into the patient's skin corresponding to movement of the patient's skin when the patient tracking apparatus is secured over the surgical site.

10. The system of claim 9, wherein the adhesive material is included with an adhesive layer, a base layer is between the adhesive layer and the plurality of surgical tracking elements, and an outer transparent layer covers the plurality of surgical tracking elements.

11. The system of claim 9, wherein the plurality of surgical tracking elements are arranged in a plurality of rows and columns.

12. The system of claim 9, wherein the plurality of surgical tracking elements are secured to the skin-based flexible patient tracking apparatus with an adhesive.

13. The system of claim 12, wherein the plurality of surgical tracking elements are molded to the skin-based flexible patient tracking apparatus.

14. The system of claim 9, wherein the surgical tracking system is an optical surgical tracking system, and the plurality of surgical tracking elements are optical surgical tracking elements viewable through the skin-based flexible patient tracking apparatus.

* * * * *

UNITED STATES PATENT AND TRADEMARK OFFICE
CERTIFICATE OF CORRECTION

| | | |
|---|---|---|
| PATENT NO. | : 11,432,896 B2 | Page 1 of 1 |
| APPLICATION NO. | : 16/572035 | |
| DATED | : September 6, 2022 | |
| INVENTOR(S) | : Marco Capote et al. | |

It is certified that error appears in the above-identified patent and that said Letters Patent is hereby corrected as shown below:

On the Title Page

Column 2, Other Publications, Line 1, delete "Reporton" and insert -- Report on -- therefor Signed and Sealed this
First Day of November, 2022

Katherine Kelly Vidal
*Director of the United States Patent and Trademark Office*